(12) United States Patent
Kamano et al.

(10) Patent No.: US 8,841,242 B2
(45) Date of Patent: Sep. 23, 2014

(54) ANTI-WEAR AGENT, ADDITIVE COMPOSITION FOR LUBRICANT, AND LUBRICANT COMPOSITION

(75) Inventors: Hideki Kamano, Ichihara (JP); Hiroaki Koshima, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 527 days.

(21) Appl. No.: 12/672,108

(22) PCT Filed: Jun. 30, 2008

(86) PCT No.: PCT/JP2008/061838
§ 371 (c)(1),
(2), (4) Date: Feb. 4, 2010

(87) PCT Pub. No.: WO2009/019941
PCT Pub. Date: Feb. 12, 2009

(65) Prior Publication Data
US 2011/0152145 A1    Jun. 23, 2011

(30) Foreign Application Priority Data

Aug. 8, 2007 (JP) ................. 2007-206888

(51) Int. Cl.
*C10M 159/18* (2006.01)
*C10M 159/12* (2006.01)
*C10M 169/04* (2006.01)

(52) U.S. Cl.
USPC ............ 508/231; 508/255; 508/279; 508/168

(58) Field of Classification Search
USPC ....................... 508/255, 257, 231, 279, 168
See application file for complete search history.

(56) References Cited

U.S. PATENT DOCUMENTS

| | | | |
|---|---|---|---|
| 3,846,319 A | 11/1974 | Hotten | |
| 4,115,288 A * | 9/1978 | Schmitt | 508/279 |
| 4,136,039 A * | 1/1979 | Jager et al. | 252/8.61 |
| 4,374,032 A | 2/1983 | Gemmill et al. | |
| 4,375,420 A * | 3/1983 | Knollmueller et al. | 252/78.3 |
| 5,145,751 A | 9/1992 | Kanai | |
| 5,334,329 A | 8/1994 | Vinci et al. | |
| 5,391,605 A | 2/1995 | Andres et al. | |
| 5,395,538 A | 3/1995 | Rudnick et al. | |
| 5,849,675 A | 12/1998 | Brown et al. | |
| 5,912,212 A * | 6/1999 | Igarashi et al. | 508/275 |
| 6,187,722 B1 | 2/2001 | Rowland et al. | |
| 6,559,106 B1 | 5/2003 | Nalesnik et al. | |
| 6,566,311 B1 | 5/2003 | Nalesnik | |
| 6,573,223 B1 * | 6/2003 | Vinci | 508/192 |
| 2004/0152817 A1 | 8/2004 | Nelson et al. | |
| 2004/0266633 A1 | 12/2004 | Negoro et al. | |
| 2006/0252658 A1 | 11/2006 | Shiraishi et al. | |
| 2007/0293406 A1 | 12/2007 | Henly et al. | |
| 2010/0184982 A1 | 7/2010 | Iwasaki et al. | |

FOREIGN PATENT DOCUMENTS

| | | |
|---|---|---|
| CN | 1791664 A | 6/2006 |
| CN | 1922125 A | 2/2007 |
| CN | 101679898 | 3/2010 |
| EP | 1 672 051 A1 | 6/2006 |
| EP | 1 672 051 A8 | 6/2006 |
| GB | 1111680 | 5/1968 |
| JP | 57 117597 | 7/1982 |
| JP | 58 103594 | 6/1983 |
| JP | 62 243692 | 10/1987 |
| JP | 64 29497 | 1/1989 |
| JP | 3 29112 | 2/1991 |
| JP | 6 072991 | 3/1994 |
| JP | 6 100881 | 4/1994 |
| JP | 6 157471 | 6/1994 |
| JP | 7 506860 | 7/1995 |
| JP | 8 165483 | 6/1996 |
| JP | 10 298574 | 11/1998 |
| JP | 2001 294879 | 10/2001 |
| JP | 2002 534436 | 10/2002 |
| JP | 2003 505577 | 2/2003 |
| JP | 2004 231654 | 8/2004 |
| JP | 2004 315703 | 11/2004 |
| JP | 2004 331950 | 11/2004 |
| JP | 2005 511816 | 4/2005 |
| JP | 2005 511817 | 4/2005 |
| JP | 2005 524762 | 8/2005 |
| JP | 2006 257383 | 9/2006 |
| JP | 2006 291042 | 10/2006 |
| JP | 2007 332377 | 12/2007 |
| JP | 2008 115267 | 5/2008 |

(Continued)

OTHER PUBLICATIONS

Ren, T., The effect of molecular structure of nitrogen-containing heterocyclic compounds on their wear properties, Chemical Abstracts, vol. 119, 184312h, (1993).
U.S. Appl. No. 12/294,457, filed Sep. 25, 2008, Koshima, et al.
Office Action issued Jul. 3, 2012 in Chinese Patent Application No. 200880102301.8.
Search Report issued Oct. 10, 2012, in European patent application No. 12176871.7.

(Continued)

*Primary Examiner* — Jim Goloboy
(74) *Attorney, Agent, or Firm* — Oblon, Spivak, McClelland, Maier & Neustadt, L.L.P.

(57) ABSTRACT

Provided are an anti-wear agent comprising a heterocyclic compound having a heterocyclic skeleton derived from a compound selected from pyridines, pyrroles, pyrimidines, pyrazoles, pyridazines, imidazoles, pyrazines, triazines, triazoles, tetrazoles, oxazoles, oxadiazoles, thiazoles, thiadiazoles, furans, dioxanes, pyrans, and thiophenes and/or comprising a reaction product of the heterocyclic compound and a compound selected from a boron compound, a molybdenum compound, and a silicon compound, which is an anti-wear agent for a lubricating oil excellent in wear resistance, friction-reducing property, and base number-retaining property, and a lubricating oil composition comprising the anti-wear agent.

6 Claims, No Drawings

(56) References Cited

FOREIGN PATENT DOCUMENTS

| WO | WO 87/07892 A2 | 12/1987 |
| WO | WO 2004/104146 A1 | 12/2004 |
| WO | 2005 080305 | 9/2005 |

OTHER PUBLICATIONS

Office Action issued Mar. 21, 2013, in Chinese patent application No. 200880102301.8.

Extended European Search Report issued Nov. 15, 2011, in Patent Application No. 08790751.5.

* cited by examiner

ANTI-WEAR AGENT, ADDITIVE COMPOSITION FOR LUBRICANT, AND LUBRICANT COMPOSITION

TECHNICAL FIELD

The present invention relates to an anti-wear agent and a lubricating oil composition comprising the anti-wear agent. More specifically, the present invention relates to an anti-wear agent having the same or better abilities of wear resistance, reducing friction, and retaining the base number than conventionally-used anti-wear agents, and to a lubricating oil composition comprising the anti-wear agent and being useful for, particularly, internal combustion engines such as a gasoline engine, a diesel engine, and a gas engine.

BACKGROUND ART

In the current automobile engines, oxidation catalysts, three-way catalysts, $NO_x$ storage reduction catalysts, diesel particulate filters (DPF's), and the like are used in order to clean the exhaust gas.

It has been known that those post-cleaning devices for the exhaust gas are adversely affected by a metal component, a phosphorous component, and a sulfur component in the engine oil, so it goes without saying that those components are preferably reduced as much as possible.

Further, reduction of the metal component, the phosphorous component, and the sulfur component in the engine oil is preferred with a view to controlling catalyst degradation.

As the anti-wear agent in the engine oil, zinc dialkyl dithiophosphate has been used for a long time and is considered to be an essential additive at present too.

The zinc dialkyl dithiophosphate contains a metal component, a phosphorous component, and a sulfur component. Therefore, the decomposed substances of the zinc dialkyl dithiophosphate become sulfuric acid and phosphorous acid, and lead to consumption of the basic compound in the engine oil, with the result that oil change intervals become extremely short. In view of the forgoing, an alternative anti-wear agent is demanded.

The same is also true of other lubricating oils except for the engine oil.

Examples of applying heterocyclic compounds to lubricating oils are described in the patent documents below.

In Patent Document 1, benzotriazole is used as a corrosion inhibitor.

Patent Document 2 describes the application of a triazole derivative to a refrigerator oil composition and insists on the effect of wear resistance.

In Patent Document 3, an imidazole fluorine derivative is used as a surface-treatment agent.

Patent Document 4 describes that polybenzoimidazole is used as a polymer including an internal lubricant.

In Patent Document 5, there is a description relating to a fluid composition for an active suspension that contains thiadiazole and benzotriazole and is excellent in wear resistance.

Patent Document 6 describes that a triazine derivative is used as a dispersant for a lubricant and a fuel.

Patent Document 7 describes an indazole thione additive used for a lubricant.

Patent Document 8 describes a fluid having low traction property and having a triazine structure.

Further, Patent Document 9 describes a wear resistant lubricant composition containing a triazine derivative.

In Patent Document 10, a substituted thiophene is used as an anti-wear agent used in a freon compressor.

Patent Document 11 describes a substituted pyridine derivative and a substituted diazine derivative as heterocyclic compounds.

However, the described compounds do not achieve a demanded wear resistance level and have problems for practical use.

Patent Document 1: JP 64-29497 A
Patent Document 2: JP 06-100881 A
Patent Document 3: JP 06-157471 A
Patent Document 4: JP 07-506860 A
Patent Document 5: JP 08-165483 A
Patent Document 6: JP 2002-534436 A
Patent Document 7: JP 2003-505577 A
Patent Document 8: JP 2004-315703 A
Patent Document 9: JP 2004-331950 A
Patent Document 10: JP 58-103594 A
Patent Document 11: JP 62-243692 A

DISCLOSURE OF THE INVENTION

An object of the present invention is to provide a heterocyclic compound having excellent wear resistance, friction-reducing property, and base number-retaining property and being useful for an anti-wear agent, a reaction product of the heterocyclic compound and a compound selected from a boron compound, a molybdenum compound, and a silicon compound, and a lubricating oil composition comprising those compounds.

The inventors of the present invention studied for developing a lubricating oil composition with improved wear resistance in view of actual conditions of the conventional technologies described above. As a result, the inventors have found out that a heterocyclic compound having a specific chemical structure and a reaction product of the heterocyclic compound and a compound selected from a boron compound, a molybdenum compound, and a silicon compound each exhibit excellent properties as an anti-wear agent, and that those compounds can impart wear resistance and the like to a lubricating oil in an internal combustion engine or a transmission engine for drive system. Then, the inventors have completed the present invention.

That is, the present invention provides:

1. an anti-wear agent comprising a heterocyclic compound which is represented by the following general formula (I) and may have a double bond in a ring part and/or a reaction product of the heterocyclic compound and a compound selected from a boron compound, a molybdenum compound, and a silicon compound;

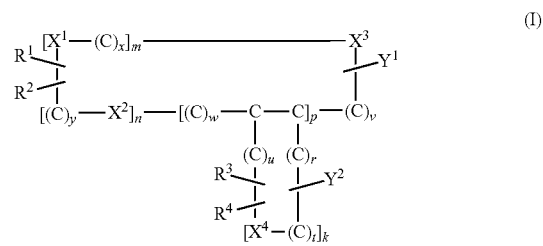

where: $X^1$, $X^2$, $X^3$, and $X^4$ each independently represent N, NH, O, or S and p represents 0 or 1; x and y each independently represent an integer of 0 to 2, u and r each independently represent an integer of 0 to 3, and t and w each independently represent an integer of 0 to 3; if p represents 0, v represents an integer of 0 to 5, and if p represents 1, v represents an integer of 0 to 3; n and m each independently represent 0 or 1, k represents an integer of 0 to 3, and if p represents 0, x, y, n, m, and v do not represent 0 simultaneously; $R^1$ to $R^4$ each independently represents a hydrogen atom bound to a carbon atom, or a hydrocarbon group which may have at least one kind of substituent selected from an amino group, an amide group, an ether group, and a carboxyl group each bound to a carbon atom; if p represents 0, $R^1$ and $R^2$ do not represent a hydrogen atom simultaneously, and if p represents 1, $R^1$ to $R^4$ do not represent a hydrogen atom simultaneously; $Y^1$ and $Y^2$ each independently represent a hydrogen atom, a halogen atom, a functional group selected from an amino group, an amide group, a hydroxy group, a carbonyl group, an aldehyde group, a carboxyl group, an ester group, and an ether group, or a hydrocarbon group which may have at least one kind of functional group selected from the functional groups and has a total carbon atoms of 1 to 150;

2. an anti-wear agent according to the above item 1, wherein p represents 0 or 1 and $X^1$, $X^2$, and $X^3$ each independently represent N, NH, O, or S in the general formula (I);

3. an anti-wear agent according to the above item 1 or 2, wherein the general formula (I) includes a heterocyclic skeleton derived from a compound selected from pyridines, pyrroles, pyrimidines, pyrazoles, pyridazines, imidazoles, pyrazines, triazines, triazoles, tetrazoles, oxazoles, oxadiazoles, thiazoles, thiadiazoles, furans, dioxanes, pyrans, and thiophenes;

4. a lubricating oil composition comprising the anti-wear agent according to any one of the above items 1 to 3;

5. a lubricating oil composition according to the above item 4, wherein the lubricating oil composition has a zinc content of 600 ppm by mass or less in terms of element based on a total amount of the lubricating oil composition;

6. a lubricating oil composition according to the above item 4, wherein the lubricating oil composition has a phosphorous content of 500 ppm by mass or less in terms of element based on a total amount of the lubricating oil composition; and 7. a lubricating oil composition according to any one of the above items 4 to 6, wherein the lubricating oil composition is for an internal combustion engine.

By using the lubricating oil composition comprising the anti-wear agent of the present invention, the heterocyclic compound and a reaction product of the heterocyclic compound and a compound selected from a boron compound, a molybdenum compound, and a silicon compound exhibits excellent wear resistance, friction-reducing property, and base number-retaining property, for example, in a gasoline engine oil, a diesel engine oil, a gas engine oil, a two-cycle engine oil, or the like in an internal combustion engine.

In addition, the heterocyclic compound and the reaction product have advantages that oil change intervals of a lubricating oil such as an engine oil can be extended and also, adverse effects on a post-cleaning device for the exhaust gas and the like and catalyst degradation are small.

BEST MODE FOR CARRYING OUT THE INVENTION

Hereinafter, the present invention is described in detail.

The anti-wear agent of the present invention is formed of a heterocyclic compound represented by the above general formula (I) and a reaction product of the heterocyclic compound and a compound selected from a boron compound, a molybdenum compound, and a silicon compound.

In the general formula (I),
(1) if p represents 0:
$X^1$, $X^2$, and $X^3$ each independently represent N, NH, O, or S;
x and y each independently represent an integer of 0 to 2 and v represents an integer of 0 to 5;
n and m each independently represent 0 or 1 and x, y, n, m, and v do not represent 0 simultaneously; and
$R^1$ and $R^2$ each independently represent a hydrogen atom bound to a carbon atom, or a hydrocarbon residue which may have at least one kind of substituent selected from an amino group, an amide group, an ether group, and a carboxyl group and $R^1$ and $R^2$ do not represent a hydrogen atom simultaneously.

In the general formula (I),
(2) if p represents 1:
$X^1$, $X^2$, $X^3$, and $X^4$ each independently represent N, NH, O, or S;
x and y each independently represent an integer of 0 to 2, u and r each independently represent an integer of 0 to 4, t and w each independently represent an integer of 0 to 3, and v represents an integer of 0 to 3; and
n and m each independently represent 0 or 1, k represents an integer of 0 to 3, and $R^1$ to $R^4$ each independently represents a hydrogen atom bound to a carbon atom, or a hydrocarbon residue which may have at least one kind of substituent selected from an amino group, an amide group, an ether group, and a carboxyl group and $R^1$ to $R^4$ do not represent a hydrogen atom simultaneously.

$Y^1$ and $Y^2$ each independently represent a hydrogen atom, a halogen atom, a functional group selected from an amino group, an amide group, a hydroxy group, a carbonyl group, an aldehyde group, a carboxyl group, an ester group, and an ether group, or a hydrocarbon group which may have at least one kind of functional group selected from the functional groups and has total carbon atoms of 1 to 150.

$R^1$ to $R^4$ each represent preferably a hydrogen atom or a hydrocarbon group having 1 to 150 carbon atoms. Specifically, $R^1$ to $R^4$ each represent a hydrocarbon group such as a methyl, ethyl, propyl, butyl, hexyl, octyl, 2-ethylhexyl, decyl, dodecyl, dodecenyl, tetradecene, tetradecenyl, hexadecene, hexadecenyl, octadecyl, octadecenyl, oleyl, stearyl, isostearyl, dococenyl, decene trimer, or polybutene group. Those may be linear or branched and saturated or unsaturated hydrocarbon groups.

$R^1$ to $R^4$ each represent more preferably a hydrocarbon group having 8 to 30 carbon atoms such as an octyl, 2-ethylhexyl, decyl, dodecyl, dodecenyl, tetradecene, tetradecenyl, hexadecene, hexadecenyl, octadecyl, octadecenyl, oleyl, stearyl, isostearyl, dococenyl, or decene trimer group.

The heterocyclic compound represented by the general formula (I) is a reaction product obtained by al lowing, for example, a compound having pyridine, pyrrole, pyrimidine, pyrazole, pyridazine, imidazole, pyrazine, triazine, triazole, tetrazole, oxazole, oxadiazole, thiazole, thiadiazole, furan, dioxane, pyran, or thiophene as a base skeleton, which serves as a base skeleton of the heterocycle, or a derivatives thereof (a) to react with a halogen compound, an amine compound, an alcohol and an epoxy compound having an alkyl group, an alkenyl group, or a cycloalkyl group each having 10 to 200 carbon atoms, or a compound having a carboxyl group (b) at a molar ratio of (a):(b) of 1:5 to 5:1 and preferably 1:2 to 2:1.

By setting the molar ratio of (a):(b) to 1:5 or more and 5:1 or less, decrease of the an active ingredient amount in the anti-wear agent of the present invention can be prevented, and there is no need to add a large amount of the anti-wear agent for securing the wear resistance, the friction-reducing property, and base number-retaining property.

Compounds (a) and (b) are reacted at room temperature to 200° C. and preferably 50 to 150° C.

The reaction may be conducted in the absence or presence of a catalyst.

In addition, a solvent, for example, an organic solvent such as hexane, toluene, xylene, tetrahydrofuran (THF), or dimethyl formamide (DMF) may be used upon the reaction.

In the heterocyclic compound represented by the general formula (I), the base skeleton of the heterocycle is a saturated or unsaturated compound in which one ring has a total number of nitrogen atoms and/or oxygen atoms and/or sulfur atoms of 1 to 4.

Examples of the cyclic compound include pyridine, pyrrole, pyrimidine, pyrazole, pyridazine, imidazole, pyrazine, triazine, triazole, tetrazole, oxazole, oxadiazole, thiazole, thiadiazole, furan, dioxane, pyran, thiophene, and their derivatives.

Preferable examples of the cyclic compound include pyridine, pyrrole, pyrimidine, pyrazole, pyridazine, imidazole, pyrazine, triazine, triazole, tetrazole, oxazole, oxadiazole, furan, dioxane, pyran, and their derivatives.

Those cyclic compounds may be monocyclic compounds described above, or polycyclic compounds such as indole, indazole, benzotriazole, benzoimidazole, purine, quinoline, isoquinoline, naphthyridine, carbazole, and naphthoimidazole.

In addition, the heterocyclic compound may be added with, as a functional group, a hydrocarbon group, amine, amide, alcohol, ketone, aldehyde, carboxylic acid, ester, ether, halogen, or a hydrocarbon compound comprising one of them. The heterocyclic compound is preferably added with a hydrocarbon group, amine, amide, alcohol, ketone, aldehyde, carboxylic acid, ester, ether, or a hydrocarbon compound comprising one of them.

Examples of the functional group added to the heterocyclic compound include methyl, ethyl, propyl, butyl, pentyl, hexyl, amine, amide, alcohol, methylcarboxy, ethylcarboxy, aldehyde, carboxylic acid, acetoxyl, propioxyl, butyroyloxyl, halogen, ethyloxy, propyloxy, ethylamine, methylamine, dimethylamine, diethylamine, polyethylenepolyamine, diethylenetriamine, triethylenetetramine, tetraethylenepentaamine, and aminoethylpiperazine.

Preferable examples of the functional group include methyl, ethyl, propyl, butyl, pentyl, hexyl, amine, amide, alcohol, methylcarboxy, ethylcarboxy, aldehyde, carboxylic acid, acetoxyl, propioxyl, butyroyloxyl, ethyloxy, propyloxy, ethylamine, methylamine, dimethylamine, diethylamine, polyethylenepolyamine, diethylenetriamine, triethylenetetraamine, tetraethylenepentaamine, and aminoethylpiperazine.

Examples of the compound (b) include: bromine-based compounds such as 2-decyl-1-bromotetradecane, 2-butyl-1-bromooctane, 2-pentyl-1-bromononane, 2-hexyl-1-bromodecane, 2-heptyl-1-bromoundecane, 2-octyl-1-bromododecane, 2-nonyl-1-bromotridecane, 2,4-dioctyl-1-bromotetradecane, bromopolybutane, bromododecane, bromotetradecane, bromohexadecane, bromooctadecane, bromoeicosane, bromodocosane, bromotetracosane, and bromoisostearyl; chlorine-based compounds such as 2-decyl-1-chlorotetradecane, 2-butyl-1-chlorooctane, 2,4-dioctyl-1-chlorotetradecane, chloropolybutane, chlorododecane, and chlorotetracosane; iodine-based compounds such as 2-decyl-1-iodotetradecane, 2-butyl-1-iodooctane, 2,4-dioctyl-1-iodotetradecane, iodopolybutene, iodododecane, andiodotetracosane; epoxycompounds such as 2-decyl-1,2-epoxytetradecane, 2-butyl-1,2-epoxyoctane, 2,4-dioctyl-1,2-epoxytetradecane, polybutene epoxide, 1,2-epoxydodecane, and 1,2-epoxytetracosane; amine compounds such as 2-decyl-tetradecylamine, 2-butyl-octylamine, 2,4-dioctyl-1-tetradecylamine, polybutenylamine, dodecylamine, and tetracosylamine; alcohols such as 2-decyl-tetradecyl alcohol, 2-butyl-octyl alcohol, 2,4-dioctyl-1-tetradecyl alcohol, polybutenyl alcohol, dodecyl alcohol, and tetracosyl alcohol; and compounds each having a carboxyl group such as 2-decyl-tetradecanoic acid, 2-butyl-ocatanoic acid, 2,4-dioctyl-1-tetradecanoic acid, polybutenyl carboxylic acid, dodecanoic acid, and tetracosanoic acid.

Those compounds may be used alone, or two or more kinds of the compounds may be used as a mixture.

In the heterocyclic compound represented by the general formula (I), if p presents 0, a cyclic structure part is derived from the above compound (a), if p represents 1, two cyclic structure parts are derived from the above compound (a).

At least one of $Y^1$ and $Y^2$ is derived from the compound (b).

The reaction product of the heterocyclic compound represented by the general formula (I) and a boron compound, which is the anti-wear agent of the present invention, is obtained by allowing the heterocyclic compound obtained as described above to react with the boron compound at a molar ratio of 1:0.01 to 10 and preferably 1:0.05 to 5.

The heterocyclic compound and the boron compound are reacted at 50 to 250° C. and preferably 100 to 200° C.

A solvent, for example, an organic solvent such as hydrocarbon oil, hexane, heptane, octane, toluene, or xylene can be used upon the reaction.

As the boron compound, for example, a boron oxide, a boron halide, boric acid, a boric anhydride, and a borate can be used.

The reaction product of the heterocyclic compound represented by the general formula (I) and a molybdenum compound, which is the anti-wear agent of the present invention, is obtained by allowing the heterocyclic compound obtained as described above to react with the molybdenum compound at a molar ratio of 1:0.01 to 10 and preferably 1:0.05 to 5.

The heterocyclic compound and the molybdenum compound are reacted at 50 to 250° C. and preferably 100 to 200° C.

A solvent, for example, an organic solvent such as hydrocarbon oil, hexane, heptane, octane, toluene, or xylene can be used upon the reaction.

As the molybdenum compound, for example, a molybdenum oxide, a molybdenum halide, or molybdic acid can be used.

Further, the reaction product of the heterocyclic compound represented by the general formula (I) and a silicon compound, which is the anti-wear agent of the present invention, is obtained by allowing the heterocyclic compound obtained as described above to react with the silicon compound at a molar ratio of 1:0.01 to 10 and preferably 1:0.05 to 5.

The heterocyclic compound and the silicon compound are reacted at 50 to 250° C. and preferably 100 to 200° C.

A solvent, for example, an organic solvent such as hydrocarbon oil, hexane, heptane, octane, toluene, or xylene can be used upon the reaction.

As the silicon compound, for example, silicon oxide, a silicon halide, silicic acid, and a silicic ester can be used.

The heterocyclic compound represented by the general formula (I) or a reaction product of the heterocyclic compound and a compound selected from a boron compound, a molybdenum compound, and a silicon compound, each of which is the anti-wear agent of the present invention obtained as described above, is mixed with a lubricating base oil, whereby the lubricating oil composition of the present invention is obtained.

The blending amount of the anti-wear agent of the present invention is 0.01 to 20 mass %, preferably 0.05 to 15 mass %, and more preferably 0.1 to 10 mass % based on the total amount of the lubricating oil composition.

By setting the blending amount to 0.01 mass % or more, abilities of wear resistance, reducing friction, and retaining the base number are exhibited. In addition, by setting the blending amount to 20 mass % or less, increase of the cost can be avoided and impair of the inherent characteristics of the lubricating base oil can be prevented.

Another additive, for example, a viscosity index improver, a pour point depressant, a detergent dispersant, an antioxidant, an anti-wear agent, an extreme pressure agent, a friction-reducing agent, a metal deactivator, a rust inhibitor, a surfactant, a demulsifier, or an antifoamer may be appropriately added to the lubricating oil composition of the present invention as required as long as the object of the present invention is not impaired.

Examples of the viscosity index improver include polymethacrylates, dispersed polymethacrylates, olefin-based copolymers (such as an ethylene-propylene copolymer), dispersed olefin-based copolymers, and styrene-based copolymers (such as a styrene-diene copolymer and a styrene-isoprene copolymer).

The blending amount of the viscosity index improver is generally about 0.5 to 15 mass % and preferably 1 to 10 mass based on the total amount of the lubricating oil composition from the viewpoint of blending effects.

Examples of the pour point depressant include polymethacrylates each having a weight average molecular weight of about 5,000 to 50,000.

The blending amount of the pour point depressant is generally about 0.1 to 2 mass % and preferably 0.1 to 1 mass % based on the total amount of the lubricating oil composition from the viewpoint of blending effects.

As the detergent dispersant, an ashless dispersant or a metal-based detergent may be used.

As the ashless dispersant, any ashless dispersants used in lubricating oils can be used, and examples of the ashless dispersant include a monotype succinimide compound represented by the general formula (II), or a bistype succinimide compound represented by the general formula (III).

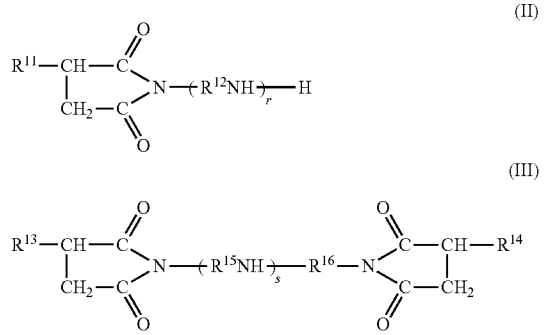

where: $R^{11}$, $R^{13}$, and $R^{14}$ each represent an alkenyl group having a number average molecular weight of 500 to 4,000 or an alkyl group having a number average molecular weight of 500 to 4,000, and $R^{13}$ and $R^{14}$ may be the same as or different from each other;

$R^{11}$, $R^{13}$, and $R^{14}$ each preferably have a number average molecular weight of 1,000 to 4,000; and in addition, $R^{12}$, $R^{15}$, and $R^{16}$ each represent an alkylene group having 2 to 5 carbon atoms, $R^{15}$ and $R^{16}$ may be the same as or different from each other, r represents an integer of 1 to 10, and s represents 0 or an integer of 1 to 10.

If $R^{11}$, $R^{13}$, and $R^{14}$ each have a number average molecular weight of less than 500, the solubility of the detergent dispersant to the base oil is lowered. If $R^{11}$, $R^{13}$, and $R^{14}$ each have a number average molecular weight exceeding 4,000, cleanability is lowered, and there is possibility that intended abilities can not be obtained.

In addition, r preferably represents an integer of 2 to 5 and more preferably 3 or 4.

If r represents less than 1, cleanability is impaired, while if r represents 11 or more, the solubility of the detergent dispersant to the base oil is impaired.

In the general formula (III), s preferably represents an integer of 1 to 4 and more preferably 2 or 3.

It is preferred that s falls within the range from the viewpoints of cleanability and solubility of the detergent dispersant to the base oil.

Examples of the alkenyl group include a polybutenyl group, a polyisobutenyl group, and an ethylene-propylene copolymer. Examples of the alkyl group include alkyl groups obtained by hydrogenating the alkenyl groups.

Typical examples of preferable alkenyl group include a polybutenyl group and a polyisobutenyl group.

The polybutenyl group is obtained by mixing 1-butene and isobutene or by polymerizing isobutene at high purity.

In addition, typical examples of preferable alkyl group include a hydrogenated polybutenyl group or a hydrogenated polyisobutenyl group.

The alkenyl or alkyl succinimide compound may be produced by allowing an alkenyl succinic anhydride obtained by a reaction of polyolefin and maleic anhydride, or an alkyl succinic anhydride obtained by hydrogenating the alkenyl succinic anhydride to react with a polyamine.

The monotype succinimide compound and bistype succinimide compound may be produced by changing a reaction ratio of the alkenyl succinic anhydride or the alkyl succinic anhydride to the polyamine.

As an olefin monomer forming the polyolefin, one kind or a mixture of two or more kinds of α-olefins each having 2 to 8 carbon atoms may be used, and a mixture of isobutene and butene-1 is preferably used.

Examples of the polyamine include single diamines such as ethylene diamine, propylene diamine, butylene diamine, and pentylene diamine, and polyalkylene polyamines such as diethylene triamine, triethylene tetramine, tetraethylene pentamine, pentaethylene hexamine, di(methylethyl)triamine, dibutylene triamine, tributylene tetramine, and pentapentylene hexamine, and piperazine derivatives such as aminoethylpiperazine.

In addition to the alkenyl or alkyl succinimide compound, a boron derivative thereof and/or a modified alkenyl or alkyl succinimide compound with an organic acid may be used.

The boron derivative of the alkenyl or alkyl succinimide compound produced by a common method may be used.

For example, the above polyolefin is allowed to react with maleic anhydride to yield an alkenyl succinic anhydride. After that, the alkenyl succinic anhydride is allowed to react with an intermediate obtained by the reaction of the above polyamine and a boron compound such as a boron oxide, a boron halide, boric acid, a boron anhydride, a borate, or an ammonium salt of boric acid, followed by imidization. As a result, a boron derivative of the alkenyl succinimide compound is obtained.

The boron content in the boron derivative is not particularly limited, but is generally 0.05 to 5 mass % and preferably 0.1 to 3 mass % in terms of boron.

The blending amount of the monotype succinimide compound represented by the general formula (II) or the bistype succinimide compound represented by the general formula (III) is 0.5 to 15 mass % and preferably 1 to 10 mass % based on the total amount of the lubricating oil composition.

If the blending amount is less than 0.5 mass %, the effect of the succinimide compound is unlikely exhibited, while if the blending amount exceeds 15 mass %, the effect comparable to the blending amount can not be obtained.

In addition, the succinimide compound may be used alone, or two or more of succinimide compounds may be used in combination as long as the above-described amount of the succinimide compound is blended.

As the metal-based detergent, any alkali earth metal-based detergent used in lubricating oils can be used. Examples thereof include alkali earth metal sulfonates, alkali earth metal phenates, alkali earth metal salicylates, and mixtures of two or more kinds thereof.

Examples of the alkali earth metal sulfonate include alkali earth metal salts of alkyl aromatic sulfonates, and in particular, magnesium salts and/or calcium salts thereof, which are obtained by sulfonating an alkyl aromatic compound having a molecular weight of 300 to 1,500 and preferably 400 to 700. Of those, calcium salts of alkyl aromatic sulfonates are preferably used.

Examples of the alkali earth metal phenate include alkali earth metal salts of alkyl phenols, alkyl phenol sulfides, or Mannich reaction products of an alkyl phenols, and in particular, magnesium salts and/or calcium salts thereof. Of those, calcium salts thereof are particularly preferably used.

Examples of the alkali earth metal salicylate include alkali earth metal salts of alkyl salicylic acids, and in particular, magnesium salts and calcium salts thereof. Of those, calcium salts thereof are preferably used.

As an alkyl group forming the alkali earth metal-based detergent, an alkyl group having 4 to 30 carbon atoms is preferred, and a linear or branched alkyl group having 6 to 18 carbon atoms is more preferred. Those may be linear or branched alkyl groups.

Those may also be primary alkyl groups, secondary alkyl groups, or tertiary alkyl groups.

In addition, examples of the alkali earth metal sulfonate, alkali earth metal phenate, and alkali earth metal salicylate include neutralized alkali earth metal sulfonates, neutralized alkali earth metal phenates, and neutralized alkali earth metal salicylates, each of which is obtained by allowing an alkyl aromatic sulfonate, an alkyl phenol, an alkyl phenol sulfide, a Mannich reaction product of an alkyl phenol, an alkyl salicylate, or the like to react directly with an oxide of an alkali earth metal such as magnesium and/or calcium or an alkali earth metal base such as a hydroxide of an alkali earth metal such as magnesium and/or calcium, or obtained by producing alkali metal salt such as a sodium salt or a potassium salt of an alkyl aromatic sulfonate, an alkyl phenol, an alkyl phenol sulfide, a Mannich reaction product of an alkyl phenol, an alkyl salicylate, or the like and thereafter, substituting the alkali metal salt by an alkali earth metal salt. Further, examples thereof include basic alkali earth metal sulfonates, basic alkali earth metal phenates, and basic alkali earth metal salicylates each obtained by heating a neutralized alkali earth metal sulfonate, a neutralized alkali earth metal phenate, or a neutralized alkali earth metal salicylate and excess amount of an alkali earth metal salt or an alkali earth metal base in the presence of water, and include perbasic alkali earth metal sulfonates, perbasic alkali earth metal phenates, and perbasic alkali earth metal salicylates each obtained by allowing a neutralized alkali earth metal sulfonate, a neutralized alkali earth metal phenate, or a neutralized alkali earth metal salicylate to react with carbonate or borate of an alkali earth metal in the presence of carbon dioxide.

As the metal-based detergent in the present invention, the above-described neutral salts, basic salts, perbasic salts, and mixtures thereof may be used. In particular, mixtures of one or more kinds of perbasic salicylates, perbasic phenates, and perbasic sulfonates, and a neutral sulfonate are preferred with a view to cleanability and wear resistance.

In the present invention, the total base number of the metal-based detergent is generally 10 to 500 mgKOH/g, and preferably 15 to 450 mgKOH/g. One kind of a metal-based detergent or two or more kinds of metal-based detergents selected from the above may be used in combination.

Note that "total base number" herein means the total base number measured by potentiometric titration (base number-perchloric acid method) in accordance with the section 7 "Petroleum products and lubricating oils-neutralization number test method" in JIS K 2501.

The metal ratio of the metal-based detergent of the present invention is not particularly limited, and generally, one kind or two or more kinds of mixture of metal-based detergents each having a metal ratio of 20 or less may be used. The lubricating oil composition of the present invention preferably includes a metal-based detergent, as an essential component, having a metal ratio of preferably 3 or less, more preferably 1.5 or less, and particularly preferably 1.2 or less in order for the lubricating oil composition of the present invention to have more excellent oxidation stability, base number-retaining property, and cleanability at high temperature.

Note that "metal ratio" herein is represented by the following expression: valence number of metal element in metal-based detergent×metal element content (mol %)/soap group content (mol %). The metal element means calcium, magnesium, or the like and the soap group means a sulfonic acid group, a phenol group, salicylic acid group, or the like.

The metal-based detergent is available in the market generally in a state where the metal-based detergent is diluted with a light lubricating base oil or the like. The metal-based detergent having a metal content of generally 1.0 to 20 mass % and preferably 2.0 to 16 mass % is preferably used.

The blending amount of the metal-based detergent is 0.01 to 20 mass % and preferably 0.1 to 10 mass % based on the total amount of the lubricating oil composition.

If the blending amount is less than 0.01 mass %, the effect of the metal-based detergent is unlikely exhibited, while if the blending amount exceeds 20 mass %, the effect comparable to the blending amount can not be obtained.

In addition, the metal-based detergent may be used alone, or two or more kinds of metal-based detergents may be used in combination as long as the above-described amount of the metal-based detergent is blended.

Examples of the antioxidant include phenol-based antioxidants, amine-based antioxidants, molybdenum amine complex-based antioxidants, and sulfur-based antioxidants.

Examples of the phenol-based antioxidant include: 4,4'-methylenebis(2,6-di-t-butylphenol); 4,4'-bis(2,6-di-t-butylphenol); 4,4'-bis(2-methyl-6-t-butylphenol); 2,2'-methylenebis(4-ethyl-6-t-butylphenol); 2,2'-methylenebis(4-methyl-6-t-butylphenol); 4,4'-butylidenebis(3-methyl-6-t-butylphenol); 4,4'-isopropylidenebis(2,6-di-t-butylphenol); 2,2'-methylenebis(4-methyl-6-nonylphenol); 2,2'-isobutylidenebis(4,6-dimethylphenol); 2,2'-methylenebis(4-methyl-6-cyclohexylphenol); 2,6-di-t-butyl-4-methylphenol; 2,6-dit-butyl-4-ethylphenol; 2,4-dimethyl-6-t-butylphenol; 2,6-di-t-amyl-p-cresol; 2,6-di-t-butyl-4-(N,N'-dimethylaminomethylphenol); 4,4'-thiobis(2-methyl-6-t-butylphenol); 4,4'-thiobis(3-methyl-6-t-butylphenol); 2,2'-thiobis(4-methyl-6-t-butylphenol); bis(3-methyl-4-hydroxy-5-t-butylbenzyl)sulfide; bis(3,5-di-t-butyl-4-hydroxybenzyl)sulfide; n-octyl-3-(4-hydroxy-3,5-di-t-butylphenyl)propionate; n-octadecyl-3-(4-hydroxy-3,5-di-t-butylphenyl)propionate; and 2,2'-thio[diethyl-bis-3-(3,5-di-t-butyl-4-hydroxyphenyl)propionate].

Of those, bisphenol-based antioxidants and ester group-containing phenol-based antioxidants are particularly preferred.

In addition, examples of the amine-based antioxidant include: monoalkyldiphenyl amine-based antioxidants such as monooctyldiphenyl amine and monononyldiphenyl amine; dialkyl diphenyl amine-based antioxidants such as 4,4'-dibutyldiphenyl amine, 4,4'-dipentyldiphenyl amine, 4,4'-dihexyldiphenyl amine, 4,4'-diheptyldiphenyl amine, 4,4'-dioctyldiphenyl amine, and 4,4'-dinonyldiphenyl amine; polyalkyldiphenyl amine-based antioxidants such as tetrabutyldiphenyl amine, tetrahexyldiphenyl amine, tetraoctyldiphenyl amine, and tetranonyldiphenyl amine; and naphthylamine-based oxidants, more specifically, alkyl substituted phenyl-α-naphthyl amines such as α-naphthyl amine, phenyl-α-naphthyl amine, butylphenyl-α-naphthyl amine, pentylphenyl-α-naphthyl amine, hexylphenyl-α-naphthyl amine, heptylphenyl-α-naphthyl amine, octylphenyl-α-naphthyl amine, and nonylphenyl-α-naphthyl amine.

Of those, dialkyldiphenyl amine-based and naphthyl amine-based antioxidants are preferred.

As the molybdenum amine complex-based antioxidant, 6-valent molybdenum compounds, more specifically, a substance obtained by reaction of molybdenum trioxide and/or molybdic acid and an amine compound may be used. For example, a compound obtained by a production method described in JP 2003-252887 A may be used.

The amine compound reacted with a 6-valent molybdenum compound is not particularly limited. Specific examples thereof include monoamines, diamines, polyamines, and alkanol amines.

More specific examples thereof include alkyl amines each having an alkyl group of 1 to 30 carbon atoms (those may be linear or branched alkyl groups) such as methyl amine, ethyl amine, dimethyl amine, diethyl amine, methylethyl amine, and methylpropyl amine; alkenyl amines each having an alkenyl group of 2 to 30 carbon atoms (those may be linear or branched alkenyl groups) such as ethenyl amine, propenyl amine, butenyl amine, octenyl amine, and oleyl amine; alkanol amines each having an alkanol group of 1 to 30 carbon atoms (those may be linear or branched alkanol groups) such as methanol amine, ethanol amine, methanolethanol amine, and methanolpropanol amine; alkylene diamines each having an alkylene group of 1 to 30 carbon atoms such as methylene diamine, ethylene diamine, propylene diamine, and butylene diamine; polyamines such as diethylene triamine, triethylene tetramine, tetraethylene pentamine, and pentaethylene hexamine; compounds in which an alkyl or alkenyl group each having 8 to 20 carbon atoms is incorporated in the above monoamine, diamine, or polyamine such as undecyldiethyl amine, undecyldiethanol amine, dodecyldipropanol amine, oleyldiethanol amine, oleyl propylene diamine, or stearyltetraethylene pentamine and heterocyclic compounds such as imidazoline; and alkylene oxide adducts thereof; and mixtures thereof.

In addition, sulfur-containing molybdenum complexes of succinimide described in JP 03-22438 B and JP 2004-2866 A are exemplified.

Examples of the sulfur-based antioxidant include phenothiazine, pentaerythritol-tetrakis-(3-laurylthiopropionate), didodecyl sulfide, dioctadecyl sulfide, didodecylthio dipropionate, dioctadecylthio dipropionate, dimyristylthio dipropionate, dodecyloctadecylthio dipropionate, and 2-mercaptobenzoimidazole.

The blending amount of the antioxidant is 0.1 to 5 mass % and preferably 0.1 to 3 mass % based on the total amount of the lubricating oil composition.

As described above, according to the present invention, a lubricating oil composition having good wear resistance, friction-reducing property, and base number-retaining property can be obtained without blending another anti-wear agent. However, another anti-wear agent may be blended as long as the object of the present invention is not impaired.

Examples of the anti-wear agent or the extreme pressure agent include: sulfur-containing compounds such as zinc dithiophosphate, zinc phosphate, zinc dithiocarbaminate, molybdenum dithiocarbaminate, molybdenum dithiophosphate, disulfides, sulfurized olefins, sulfurized fats and oils, sulfurized esters, thiocarbonates, thiocarbamates, and polysulfides; phosphorous-containing compounds such as phosphites, phosphates, phosphonate, and amine salts and metal salts thereof; and anti-wear agents each containing sulfur and phosphorous such as thiophosphites, thiophosphates, thiophosphonates, and amine salts and metal salts thereof.

When another anti-wear agent or another extreme pressure agent is blended as required, the blending amount of the other anti-wear agent is 600 ppm by mass or less in terms of zinc element based on the total amount of the lubricating oil composition.

Preferred is 0 to 500 ppm by mass and more preferred is 0 to 400 ppm by mass.

In addition, the blending amount of the other anti-wear agent or extreme pressure agent is 500 ppm by mass or less in terms of phosphorous element based on the total amount of the lubricating oil composition.

Preferred is 0 to 400 ppm by mass and more preferred is 0 to 300 ppm by mass.

When the blending amount of zinc is 600 ppm by mass or less and the blending amount of phosphorous is 500 ppm by mass or less, oil exchange intervals are not shortened extremely due to consumption of basic compounds in the lubricating oil composition, for example, an engine oil.

As the friction-reducing agent, any compound generally used as a friction-reducing agent for lubricating oil can be used. Examples thereof include ashless friction-reducing agents such as fatty acid esters, fatty acid amides, fatty acids, aliphatic alcohols, aliphatic amines, and aliphatic ethers each having at least one alkyl or alkenyl group of 6 to 30 carbon atoms in the molecules.

The blending amount of the friction-reducing agent is 0.01 to 2 mass and preferably 0.01 to 1 mass % based on the total amount of the lubricating oil composition.

Examples of the metal deactivator include benzotriazole-based, tolyltriazole-based, thiadiazole-based, and imidazole-based compounds.

The blending amount of the metal deactivator is 0.01 to 3 mass % and preferably 0.01 to 1 mass % based on the total amount of the lubricating oil composition.

Examples of the rust inhibitor include petroleum sulfonates, alkyl benzene sulfonates, dinonylnaphthalene sulfonates, alkenyl succinates, and polyalcohol esters.

The blending amount of the rust inhibitor is generally about 0.01 to 1 mass and preferably 0.05 to 0.5 mass based on the total amount of the lubricating oil composition from the viewpoint of blending effects.

Examples of the surfactant or demulsifier include polyalkylene glycol-based nonionic surfactants such as polyoxyethylene alkyl ether, polyoxyethylene alkylphenyl ether, and polyoxyethylene alkylnaphthyl ether.

The blending amount of the surfactant or demulsifier is 0.01 to 3 mass % and preferably 0.01 to 1 mass % based on the total amount of the lubricating oil composition.

Examples of the antifoamer include a silicone oil, a fluorosilicone oil, and a fluoroalkyl ether. The blending amount of the antifoamer is 0.005 to 0.5 mass % and preferably 0.01 to 0.2 mass % based on the total amount of the lubricating oil composition from the viewpoint of balance between antifoaming effect and economical efficiency.

The lubricating base oil in the lubricating oil composition of the present invention is not particularly limited, and base oils appropriately selected from any one of mineral oils and synthetic oils generally used in the base oil of the lubricating oil for internal combustion engine may be used.

The mineral oils each obtained as described in the following are exemplified. An atmospheric residue oil obtained by atmospheric distillation of the crude oil is distilled off under reduced pressure to obtain a lubricating oil fraction. The thus obtained lubricating oil fraction is refined by one or more processes of solvent deasphalting, solvent extraction, hydrocracking, solvent dewaxing, catalytic dewaxing, and hydrogenation refining, whereby a mineral oil is obtained. Alternatively, mineral oils each produced by isomerizing a wax, GTL, and WAX are exemplified.

On the other hand, examples of the synthetic oil include polybutene, polyolefins [α-olefin homopolymers and copolymers (such as an ethylene-α-olefin copolymer) and the like], various esters (such as polyol esters, dibasic acid esters, and phosphates), various ethers (such as polyphenyl ethers), polyglycol, alkyl benzene, and alkyl naphthalene. Of those synthetic oils, polyolefins and polyesters are particularly preferred.

In the present invention, as a base oil, one kind of the mineral oil may be used alone or two or more kinds of the mineral oils may be used in combination.

Alternatively, one kind of the synthetic oil may be used and two or more kinds of the synthetic oils may be used in combination.

Further, one or more kinds of mineral oils and one or more kinds of synthetic oils may be used in combination.

The viscosity of the base oil is not particularly limited and varies depending on use of the lubricating oil composition. In general, the kinematic viscosity at 100° C. is generally 2 to 30 mm²/s, preferably 3 to 15 mm²/s, and particularly preferably 4 to 10 mm²/s.

If the kinematic viscosity at 100° C. is 2 mm²/s or more, evaporation loss is small, and if the kinematic viscosity at 100° C. is 30 mm²/s or less, power loss owing to viscosity resistance is suppressed, whereby an effect of improving fuel consumption can be obtained.

In addition, a base oil having % $C_A$ of 3.0 or less by a ring analysis and a sulfur content of 50 ppm by mass or less is preferably used.

Here, "% $C_A$ by a ring analysis" denotes a ratio (percentage) of an aromatic content calculated by an n-d-M ring analysis method.

In addition, the sulfur content is measured in accordance with JIS K 2541.

The base oil having % $C_A$ of 3.0 or less and a sulfur content of 50 ppm by mass or less has good oxidation stability, and a lubricating oil composition capable of suppressing increase of an acid number and generation of sludge can be provided.

% $C_A$ is more preferably 1.0 or less, still more preferably 0.5 or less, and the sulfur content is more preferably 30 ppm by mass or less.

Further, the viscosity index of the base oil is preferably 70 or more, more preferably 100 or more, and still more preferably 120 or more.

The viscosity change owing to temperature change of the base oil having a viscosity index of 70 or more is small.

The substance in which the anti-wear agent of the present invention is blended with a lubricating oil fraction of a hydrocarbon oil or a synthetic oil, or a mixture thereof can be used as a lubricating oil composition for an internal combustion engine (such as a lubricating oil for a gasoline engine, a lubricating oil composition for a diesel engine, and a lubricating oil composition for a gas engine), a gear oil, a bearing oil, a change gear oil, a shock absorber oil, grease, a wet brake oil, a hydraulic oil, a turbine oil, a compressor oil, or a refrigerator oil.

EXAMPLES

Hereinafter, the present invention is described in detail by way of examples and comparative examples, but the present invention is not limited to those examples.

Synthetic Example 1

1.3 g (0.055 mol) of NaH and 100 ml of dimethyl formamide (DMF) were put in a 500-ml flask.

Next, 5.0 g (0.05 mol) of 3,5-diamino-1,2,4-triazole dissolved in 100 ml of DMF were dropped to the mixture, followed by a reaction at 100° C. for 2 hours.

Next, 16.6 g (0.05 mol) of oleyl bromide were dropped to the reacted mixture, followed by a reaction at 100° C. for 4 hours.

After distillation of DMF, the resultant mixture was dissolved in 200 ml of toluene and washed with water.

The resultant was dried with magnesium sulfate and toluene was distilled off, whereby 15 g of a mixture of 1-oleyl-3,5-diamino-1,2,4-triazole and 4-oleyl-3,5-diamino-1,2,4-triazole (referred to as Anti-wear Agent A) were obtained.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents an oleyl group and the other one represents hydrogen; and both $Y^1$ and $Y^2$ each represent an amino group.

Synthetic Example 2

5.0 g (0.05 mol) of 3,5-diamino-1,2,4-triazole, 5.3 g (0.053 mol) of triethylamine, and 200 ml of THF were put in a 500-ml flask, and then refluxed and stirred.

15.0 g (0.05 mol) of oleic acid chloride dissolved in 50 ml of THF were dropped to the mixture, followed by a reaction for 4 hours.

The reacted mixture was filtered and THF was distilled off, and thereafter, the resultant was dissolved in 200 ml of toluene and washed with water.

After the resultant mixture was dried with magnesium sulfate, toluene was distilled off, whereby a heterocyclic compound was obtained. The yield of the obtained heterocyclic compound (referred to as Anti-wear Agent B) was 16 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents an oleic acid amide group and the other one represents hydrogen; $Y^1$ represents an amino group; and $Y^2$ represents hydrogen.

Synthetic Example 3

The reaction was performed in the same manner as Synthetic Example 2 except that 4.2 g (0.05 mol) of 3-amino-1,2,4-triazole were used instead of 3,5-diamino-1,2,4-triazole.

The yield of the obtained heterocyclic compound (referred to as Anti-wear Agent C) was 16 g.

The structure of the main component in the obtained heterocyclic compound is represented by the general formula (I) where: p represents 0; both m and n each represent 1; all of $X^1$, $X^2$ and $X^3$ each represent N; one of x, y, and v represents 0; two others each represent 1; one of $R^1$ and $R^2$ represents an oleic acid amide group and the other one represents hydrogen; and $Y^1$ and $Y^2$ each represent hydrogen.

Synthetic Example 4

The reaction was performed in the same manner as Synthetic Example 2 except that 6.7 g (0.05 mol) of 6-aminoindazole were used instead of 3,5-diamino-1,2,4-triazole. The yield of the obtained heterocyclic compound (referred to as Anti-wear Agent D) was 17 g.

The structure of the main component in the obtained heterocyclic compound is represented by the general formula (I) where: p, m, n, and k represent 1, 1, 0, and 0, respectively; $X^1$ and $X^3$ each represent N; x, v, w, and u represent 0, 1, 0, and 4, respectively; $R^1$ and $R^2$ each represent hydrogen; one of $R^3$ and $R^4$ represents an oleic acid amide group and the other one represents hydrogen; and $Y^1$, $Y^2$, and $Y^3$ each represent hydrogen.

Synthetic Example 5

The reaction was performed in the same manner as Synthetic Example 2 except that 15.1 g (0.05 mol) of heptylundecanoic acid chloride were used instead of oleic acid chloride.

The yield of the obtained heterocyclic compound (referred to as Anti-wear Agent E) was 17 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0, two others each represent 1; one of $R^1$ and $R^2$ represents a heptylundecanoic amide group and the other one represents hydrogen; and $Y^1$ and $Y^2$ each represent hydrogen.

Synthetic Example 6

The reaction was performed in the same manner as Synthetic Example 2 except that 6.4 g (0.05 mol) of 2-aminouracil were used instead of 3,5-diamino-1,2,4-triazole.

The yield of the obtained heterocyclic compound (referred to as Anti-wear Agent F) was 17 g.

The structural formula of the main component in the obtained heterocyclic compound is a mixture of a compound represented by the general formula (I) where: p, m, n, and v represent 0, 1, 0, and 3, respectively; $X^1$ and $X^3$ each represent N; x represents 1; one of $R^1$ and $R^2$ represents an oleic acid amide group and the other one represents hydrogen; and $Y^1$ and $Y^2$ each represent a hydroxy group and a compound represented by the general formula (I) where: p, m, n, and v represent 0, 1, 0, and 3, respectively; $X^1$ and $X^3$ each represent N; x represents 1; one of $R^1$ and $R^2$ represents an oleyl ether group and the other one represents hydrogen; and $Y^1$ represents a hydroxy group and $Y^2$ represents an amino group.

Synthetic Example 7

The reaction was performed in the same manner as Synthetic Example 2 except that 6.4 g (0.05 mol) of 5,5-dimethyl hydantoin were used instead of 3,5-diamino-1,2,4-triazole.

The yield of the obtained heterocyclic compound (referred to as Anti-wear Agent G) was 16 g.

The structural formula of the main component in the obtained heterocyclic compound is represented by the general formula (I) where: p, m, and n represent 0, 1, and 0, respectively; $X^1$ and $X^3$ each represent N; x and v represent 1 and 2, respectively; one of $R^1$ and $R^2$ represents an oleic acid amide group and the other one represents hydrogen; and $Y^1$ represents two carbonyl groups and $Y^2$ represents two methyl groups.

Synthetic Example 8

The reaction was performed in the same manner as Synthetic Example 2 except that 5.2 g (0.05 mol) of glycerol formal were used instead of 3,5-diamino-1,2,4-triazole.

The yield of the obtained heterocyclic compound (referred to as Anti-wear Agent H) was 15 g.

The structure of the main component in the obtained heterocyclic compound is represented by the general formula (I) where: p, m, and n represent 0, 1, and 0, respectively; $X^1$ and $X^3$ each represent O; x and v represent 3 and 1, respectively; one of $R^1$ and $R^3$ represents an oleyl ether group and the other one represents hydrogen; and $Y^1$ and $Y^2$ each represent hydrogen.

Synthetic Example 9

The reaction was performed in the same manner as Synthetic Example 2 except that 7.1 g (0.05 mol) of kojic acid were used instead of 3,5-diamino-1,2,4-triazole.

The yield of the obtained heterocyclic compound (referred to as Anti-wear Agent I) was 16 g.

The structure of the main component in the obtained heterocyclic compound is a mixture of a compound represented by the general formula (I) where: p, m, and n each represent 0; $X^3$ represents O; v represents 5; one of $R^1$ and $R^2$ represents an oleyl methyl ether group and the other one represents hydrogen; and $Y^1$ represents a hydroxy group and $Y^2$ represents a carbonyl group, and a compound represented by the general formula (I) where: p, m, and n each represent 0; $X^3$ represents O; v represents 5; one of $R^1$ and $R^2$ represents an oleyl ether group and the other one represents hydrogen; and $Y^1$ represents a hydroxymethyl group and $Y^2$ represents a carbonyl group.

Synthetic Example 10

The reaction was performed in the same manner as Synthetic Example 2 except that 24.3 g (0.05 mol) of tridecanoic acid chloride were used instead of oleic acid chloride.

The yield of the obtained heterocyclic compound (referred to as Anti-wear Agent J) was 26 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents a tridecanoic acid amide group and the other one represents hydrogen; and $Y^1$ represents an amino group and $Y^2$ represents hydrogen.

Synthetic Example 11

The reaction was performed in the same manner as Synthetic Example 2 except that 20.7 g (0.05 mol) of polyisobutanoic acid (weight average molecular weight Mw of 350) chloride were used instead of oleic acid chloride.

The yield of the obtained heterocyclic compound (referred to as Anti-wear Agent K) was 23 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents a polyisobutanoic acid amide group and the other one represents hydrogen; $Y^1$ represents an amino group and $Y^2$ represents hydrogen.

Synthetic Example 12

The reaction was performed in the same manner as Synthetic Example 1 except that 4.2 g (0.05 mol) of 3-amino-1,2,4-triazole were used instead of 3,5-diamino-1,2,4-triazole.

The yield of the obtained heterocyclic compound (referred to as Anti-wear Agent L) was 14 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents an oleyl group and the other one represents hydrogen; and $Y^1$ represents an amino group and $Y^2$ represents hydrogen.

Synthetic Example 13

The reaction was performed in the same manner as Synthetic Example 1 except that 6.7 g (0.05 mol) of 6-aminoindazole were used instead of 3,5-diamino-1,2,4-triazole.

The yield of the obtained heterocyclic compound (referred to as Anti-wear Agent M) was 16 g.

The structure of the main component in the obtained heterocyclic compound is represented by the general formula (I) where: p, m, n, and k represent 1, 1, 0, and 0, respectively; $X^1$ and $X^3$ each represent N; x, v, w, and u represent 0, 1, 0, and 4, respectively; one of $R^1$ and $R^2$ each represent an oleyl group and the other one represents hydrogen; $R^3$ and $R^4$ each represent hydrogen; $Y^1$ represents hydrogen; and one of $Y^2$ and $Y^3$ represents an amino group and the other one represents hydrogen.

Synthetic Example 14

1.3 g (0.055 mol) of NaH and 100 ml of xylene were put in a 500-ml flask.

Next, 17.5 g (0.05 mol) of the compound obtained in Synthetic Example 1 dissolved in 100 ml of xylene were dropped to the resultant mixture, followed by a reaction at 100° C. for 2 hours.

Next, 6.9 g (0.055 mol) of 2-bromoethanol were dropped to the reacted mixture, followed by a reaction at 100° C. for 4 hours.

After the reaction product was washed with water and dried, xylene was distilled off. As a result, a heterocyclic compound was obtained.

The yield of the obtained heterocyclic compound (referred to as Anti-wear Agent N) was 22 g.

The structure of the main component in the obtained heterocyclic compound is represented by the general formula (I) where: p represents 0; both m and n each represent 1; all of $X^1$, $X^2$, and $X^3$ each represent N; one of x, y, and v represents 0 and two others each represent 1; one of $R^1$ and $R^2$ represents an oleyl group and the other one represents hydrogen; and $Y^1$ represents a 2-hydroxyethylamino group; and $Y^2$ represents hydrogen.

Synthetic Example 15

The reaction was performed in the same manner as Synthetic Example 14 except that 6.8 g (0.055 mol) of 2-bromoethyl amine were used instead of 2-bromoethanol.

The yield of the obtained heterocyclic compound (referred to as Anti-wear Agent O) was 17 g.

The structure of the main component in the obtained heterocyclic compound is represented by the general formula (I) where: p represents 0; both m and n each represent 1; all of $X^1$, $X^2$, and $X^3$ each represent N; one of x, y, and v represents 0 and two others each represent 1; one of $R^1$ and $R^2$ represents an oleyl group and the other one represents hydrogen; $Y^1$ represents a 2-aminoethyl amino group; and $Y^2$ represents hydrogen.

Synthetic Example 16

69.9 g (0.2 mol) of 1-oleyl-3,5-diamino-1,2,4-triazole obtained by the method for Synthetic Example 1 and 6.2 g (0.1 mol) of boric acid were put in a 200-ml flask, followed by a reaction at 80° C. for 1 hour in a stream of nitrogen.

Next, the temperature was increased to 150° C., followed by a reaction for 3 hours.

Water was distilled off under reduced pressure, whereby the yield of the obtained heterocyclic compound (referred to as Anti-wear Agent P) was 72 g.

The boron content of the product was 1.5 wt %.

Synthetic Example 17

69.9 g (0.2 mol) of 1-oleyl-3,5-diamino-1,2,4-triazole obtained by the method for Synthetic Example 1 and 7.2 g (0.05 mol) of molybdenum trioxide, and 3.6 g (0.2 mol) of water were put in a 200-ml flask, followed by a reaction at 80° C. for 1 hour in a stream of nitrogen.

Next, the temperature was increased to 100° C., followed by a reaction for 3 hours.

Water was distilled off under reduced pressure, whereby the yield of the obtained heterocyclic compound (referred to as Anti-wear Agent Q) was 74 g.

The molybdenum content of the product was 6.3 wt %.

Synthetic Example 18

The reaction was performed in the same manner as Synthetic Example 2 except that 5.9 g (0.05 mol) of glycerol carbonate were used instead of 3,5-diamino-1,2,4-triazole.

The yield of the obtained heterocyclic compound (referred to as Anti-wear Agent R) was 15 g.

The structure of the main component in the obtained heterocyclic compound is represented by the general formula (I) where: p, m, and n represents 0, 1, and 0, respectively; $X^1$ and $X^3$ each represent O; x represents 2 and v represents 1; one of $R^1$ and $R^2$ represents a 9-octadecenyl carboxymethyl group and the other one represents hydrogen; and $Y^1$ represents an oxo group.

Synthetic Example 19

The reaction was performed in the same manner as Synthetic Example 3 except that 15.1 g (0.05 mol) of heptylundecanoic acid chloride were used instead of oleic acid chloride. The yield of the obtained heterocyclic compound (referred to as Anti-wear Agent S) was 17 g.

The structure of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents a heptylundecanoic acid amide group and the other one represents hydrogen; and $Y^1$ represents hydrogen.

Synthetic Example 20

A 500-ml flask was filled with 18.4 g (0.1 mol) of cyanuric chloride (2,4,6-trichloro-1,3,5-triazine), 180 ml of acetone, 20 ml of water, and 27.7 g (0.33 mol) of sodium hydrogen carbonate, the atmosphere in the flask was replaced with nitrogen by stirring, and the flask was kept at 0° C.

26.7 g (0.1 mol) of oleyl amine were dropped to the mixture, followed by a reaction for 1 hour.

Next, 7.5 g (0.11 mol) of ammonia water ($NH_3$; 25 mass %) were added to the reacted mixture, followed by a reaction at 50° C. for 2 hours.

Further, the reacted mixture was transferred to an autoclave and 7.5 g of ammonia water ($NH_3$; 25 mass %) (0.11 mol) were added thereto, followed by a reaction at 100° C. for 2 hours.

The reacted mixture was filtered and acetone/water was distilled off.

The yield of the obtained heterocyclic compound (referred to as Anti-wear Agent T) was 32 g.

The structure of the main component in the obtained heterocyclic compound is represented by the general formula (I) where: p represents 0; both m and n each represent 1; all of $X^1$, $X^2$, and $X^3$ each represent N; all of x, y, and v represent 1; one of $R^1$ and $R^2$ represents an oleyl amino group and the other one represents hydrogen; and both $Y^1$ and $Y^2$ each represent an amino group.

Synthetic Example 21

A 500-ml flask was filled with 28.2 g (0.1 mol) of oleic acid, 7.2 g (0.12 mol) of ethylene diamine, and 100 ml of toluene, and the mixture was dehydrated by reaction at 110° C. in a stream of nitrogen.

Next, while toluene was distilled off, the temperature was increased to 230° C., followed by a reaction for 2 hours. The yield of the obtained heterocyclic compound (referred to as Anti-wear Agent U) was 31 g.

The structure of the main component in the obtained heterocyclic compound is represented by the general formula (I) where: p, m, and n represent 0, 1, and 0, respectively; $X^1$ and $X^3$ each represent N; x and v each represent 1; one of $R^1$ and $R^2$ represent an 8-hexadecenyl group and the other one represents hydrogen; and $Y^1$ represents hydrogen.

Synthetic Example 22

The reaction was performed in the same manner as Synthetic Example 1 except that 3.5 g (0.05 mol) of 1,2,4-triazole were used instead of 3,5-diamino-1,2,4-triazole.

The yield of the obtained heterocyclic compound (referred to as Anti-wear Agent V) was 13 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represents 0 and two others each represent 1; one of $R^1$ and $R^2$ represents an oleyl group and the other one represents hydrogen; and $Y^1$ represents hydrogen.

Synthetic Example 23

7.4 g (0.073 mol) of diisopropyl amine and 100 ml of THF were put in a 500-ml flask.

44 ml of butyl lithium (1.67 M hexane solution; 0.073 mol) were dropped thereto at −30° C. and the mixture was stirred at the same temperature for 30 minutes.

Next, 5.1 g (0.055 mol) of γ-picoline in THF solution (80 ml) were added and the mixture was stirred at −10° C. for 1 hour and 30 minutes.

Next, 15.0 g (0.036 mol) of 2-decyl-1-bromotetradecane in THF solution (80 ml) were dropped to the mixture, followed by a reaction at room temperature for 1 hour and at 40° C. for 4 hours.

After a saturated ammonium chloride solution was added to the reacted mixture, the organic layer was extracted with hexane and dried with magnesium sulfate.

The solvent was distilled off and a heterocyclic compound was purified by silica gel column chromatography.

The yield of the obtained heterocyclic compound (referred to as Anti-wear Agent W) was 8 g.

The structural formula of the main component in the obtained heterocyclic compound is represented by the general formula (I) where: all p, m, and n each represent 0; $X^3$ represents N; v represents 5; one of $R^1$ and $R^2$ represents a 2-decyltetradecyl group and the other one represents hydrogen; and $Y^1$ represents hydrogen.

Synthetic Example 24

1.4 g (0.037 mol) of NaH and 20 ml of DMF were put in a 500-ml flask.

4.2 g (0.036 mol) of benzoimidazole dissolved in 30 ml of DMF were dropped to the mixture, followed by a reaction at room temperature for 30 minutes.

Next, 12.6 g (0.03 mol) of 2-decyl-1-bromotetradecane dissolved in 15 ml of toluene were dropped to the reacted mixture, followed by a reaction at 100° C. for 7 hours.

After distillation of the solvent, the resultant mixture was dissolved in 300 ml of hexane and washed with water.

The resultant was dried with magnesium sulfate and hexane was distilled off, whereby a heterocyclic compound was purified by silica gel column chromatography.

The yield of the obtained heterocyclic compound (referred to as Anti-wear Agent X) was 8 g.

The structure of the main component in the obtained heterocyclic compound is represented by the general formula (I) where: p, m, n, and k represent 1, 1, 0, and 0, respectively; $X^1$ and $X^3$ each represent N; x, v, and w each represent 1, the sum of u and r is 4; one of $R^1$ and $R^2$ represents a 2-decyltetradecyl group and the other one represents hydrogen; $R^3$ and $R^4$ each represent hydrogen; $Y^1$ represents an amino group; and both $Y^2$ and $Y^3$ each represent hydrogen.

Synthetic Example 25

23.5 g (0.05 mol) of 1-(2-decyltetradecyl)benzoimidazole obtained by the method for Synthetic Example 24 and 1.6 g (0.025 mol) of boric acid were put in a 200-ml flask, followed by a reaction at 80° C. for 1 hour in a stream of nitrogen.

Next, the temperature was increased to 150° C., followed by a reaction for 3 hours.

Water was distilled off under reduced pressure, whereby the yield of the obtained heterocyclic compound (referred to as Anti-wear Agent Y) was 23 g.

The boron content of the product was 1.0 wt %.

Synthetic Example 26

56.5 g (0.2 mol) of oleic acid, 28.4 g (0.21 mol) of aminoguanidine bicarbonate, 20 ml of water, and 100 ml of xylene were put in a 500-ml flask, followed by a reaction at 100° for 1 hour in a stream of nitrogen.

Next, while water and xylene were removed, the temperature was increased to 180° C., followed by a reaction for 5 hours.

The yield of the obtained heterocyclic compound (referred to as Anti-wear Agent Z) was 76 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represent 0 and two others each represent 1; one of $R^1$ and $R^2$ represents an oleyl group and the other one represents hydrogen; and $Y^1$ represents an amino group.

Synthetic Example 27

32.0 g (0.1 mol) of 1-(8-heptadecenyl)-3-amino-1,2,4-triazole obtained by the method for Synthetic Example 26 and 1.6 g (0.025 mol) of boric acid were put in a 200-ml flask, followed by a reaction at 80° C. for 1 hour in a stream of nitrogen.

Next, the temperature was increased to 150° C., followed by a reaction for 3 hours.

Water was distilled off under reduced pressure, whereby the yield of the obtained heterocyclic compound (referred to as Anti-wear Agent AA) was 31 g.

The boron content of the product was 0.8 wt %.

Synthetic Example 28

The reaction was performed in the same manner as Synthetic Example 1 except that 9.7 g (0.05 mol) of 2-ethylhexyl bromide were used instead of oleyl bromide.

The yield of the obtained heterocyclic compound (referred to as Anti-wear Agent AB) was 12 g.

The structural formula of the main component in the obtained heterocyclic compound is represented by the general formula (I) where: p represents 0; both m and n each represent 1; all of $X^1$, $X^2$ and $X^3$ each represent N; one of x, y, and v represent 0 and two others each represent 1; one of $R^1$ and $R^2$ represents a 2-ethylhexyl group and the other one represents hydrogen; and both $Y^1$ and $Y^2$ each represent an amino group.

Synthetic Example 29

21.1 g (0.1 mol) of 1-(2-ethylhexyl)-3-amino-1,2,4-triazole obtained by the method for Synthetic Example 28 and 1.6 g (0.025 mol) of boric acid were put in a 200-ml flask, followed by a reaction at 80° C. for 1 hour in a stream of nitrogen.

Next, the temperature was increased to 150° C., followed by a reaction for 3 hours.

Water was distilled off, whereby the yield of the obtained heterocyclic compound (referred to as Anti-wear Agent AC) was 21 g.

The boron content of the product was 1.1 wt %.

Examples 1 to 31 and Comparative Examples 1 to 3

The respective components described in Table 1 (Anti-wear Agents A to AC) and 2-(aminomethyl)pyridine were blended at respective ratios described in Table 1, whereby each lubricating oil composition was prepared.

Abilities of those lubricating oil compositions were evaluated by a Shell four-ball wear test and a reciprocating friction wear test described later.

The obtained results are shown in Table 1.

Example 32 and Comparative Examples 4 and 5

The respective components described in Table 2 were blended at respective ratios described in Table 2, whereby each lubricating oil composition was prepared.

Abilities of those lubricating oil compositions were evaluated by a Shell four-ball wear test, a reciprocating friction wear test, and an oxidative stability test described later.

The obtained results are shown in Table 2.

[Shell Four-Ball Wear Test]

A wear test was conducted in accordance with ASTM D2783 using a ½-inch ball formed of SUJ-2 as a test ball under the following condition: rotation frequency of 1,200 rpm; load of 294 N; temperature of 80° C.; and period of 30 minutes. Then, a wear scar diameter of the test ball after the wear test was measured.

As the wear scar diameter of the test ball after the wear test is smaller, anti-wear resistance is demonstrated to be excellent when

[Reciprocating Friction Wear Test]

A wear test was conducted by using a plate formed of SUJ-2 having a hardness (HRC) of 61, a surface roughness (Rz) of 0.042 μm and measuring 3.9 mm thick by 38 mm wide by 58 mm long and by using a 10-mm ball formed of SUJ-2 as a test ball under the following condition: load of 50 N; amplitude of 15 mm; frequency of 5 Hz; temperature of 100° C.; and period of 30 minutes. Then, a wear scar width after the wear test was measured.

As the wear scar diameter of the test ball after the wear test is smaller, the anti-wear resistance is demonstrated to be excellent.

In addition, a frictional coefficient was also measured.

As the frictional coefficient is smaller, friction-reducing property is demonstrated to be excellent.

[Oxidative Stability Test]

The base number of the lubricating oil composition before and after the test was measured by conducting Indiana stirring oxidation test according to JIS K2514-1996 in the following condition, whereby a residual ratio of the base number was determined:

test temperature, 165.5° C.; rotation frequency, 1,300 rpm; test period, 48 hours; and catalysts, copper plate and iron plate.

The residual ratio of the base number was calculated by the following formula.

Residual ratio of base number(%)=(base number of lubricating oil composition after test/base number of the lubricating oil composition before test)×100

As the residual ratio of the base number is larger, the long drain property is demonstrated to be excellent and oil change intervals are demonstrated to be long.

The properties of respective lubricating oil compositions were measured as follows.

(Calcium Content)

The calcium content was measured in accordance with JIS-5S-38-92.

(Phosphorous Content)

The phosphorous content was measured in accordance with JPI-5S-38-92.

(Sulfur Content)

The sulfur content was measured in accordance with JIS K2541.

(Sulfated Ash Content)

The sulfated ash content was measured in accordance with JIS K2272.

The respective components used in Tables 1 and 2 are as follows.

1. Anti-wear Agents A to AC obtained in Synthetic Examples 1 to 29; 2-(aminomethyl)pyridine manufactured by SIGMA-ALDRICH Corp. (corresponding to examples in Cited document 11)
2. Base oil: hydrogenated and refined base oil, kinematic viscosity at 40° C.; 21 mm$^2$/s, kinematic viscosity at 100° C.; 4.5 mm$^2$/s, viscosity index; 127, % CA (% CA; by an n-d-M ring analysis); 0.0, sulfur content; less than 20 ppm by mass, and evaporated NOACK amount (standard of The Japan Petroleum Institute PI-5S-41-93); 13.3 mass %
3. Metal-based detergent: perbasic calcium salicylate, base number (perchloric acid method); 225 mgKOH/g, calcium content; 7.8 mass %, and sulfur content; 0.3 mass %
4. Ashless detergent: polybutenyl succinimide, number average molecular weight of polybutenyl groups; 1,000, and nitrogen content; 2.0 mass %
5. Anti-wear Agent: zinc dialkyl dithiophosphate, alkyl groups; a mixture of a secondary butyl group and a secondary hexyl group, Zn content; 9.0 mass %, phosphorous content; 8.2 mass %, sulfur content; 17.1 mass %, and alkyl groups; a mixture of a secondary butyl group and a secondary hexyl group

TABLE 1

| | | | Example | | | | | | | | | |
|---|---|---|---|---|---|---|---|---|---|---|---|---|
| | | | 1 | 2 | 3 | 4 | 5 | 6 | 7 | 8 | 9 |
| Lubricating oil composition | Blending amount (mass %) | Base oil | 99.00 | 97.00 | 95.00 | 99.00 | 99.00 | 99.00 | 99.00 | 99.00 | 99.00 |
| | | Zinc dialkyl dithiophosphate | 0.00 | 0.00 | 0.00 | 0.00 | 0.00 | 0.00 | 0.00 | 0.00 | 0.00 |
| | | Anti-wear Agent A | 1.00 | 3.00 | 5.00 | | | | | | |
| | | Anti-wear Agent B | | | | 1.00 | | | | | |
| | | Anti-wear Agent C | | | | | 1.00 | | | | |
| | | Anti-wear Agent D | | | | | | 1.00 | | | |
| | | Anti-wear Agent E | | | | | | | 1.00 | | |
| | | Anti-wear Agent F | | | | | | | | 1.00 | |
| | | Anti-wear Agent G | | | | | | | | | 1.00 |
| | | Anti-wear Agent H | | | | | | | | | |
| | | Anti-wear Agent I | | | | | | | | | |
| | | Anti-wear Agent J | | | | | | | | | |
| | | Anti-wear Agent K | | | | | | | | | |
| | | Anti-wear Agent L | | | | | | | | | |
| | | Anti-wear Agent M | | | | | | | | | |
| | | Anti-wear Agent N | | | | | | | | | |
| | | Anti-wear Agent O | | | | | | | | | |
| | | Total | 100.00 | 100.00 | 100.00 | 100.00 | 100.00 | 100.00 | 100.00 | 100.00 | 100.00 |
| Test result | property and the like of composition (mass %) | Phosphorous content | 0 | 0 | 0 | 0 | 0 | 0 | 0 | 0 | 0 |
| | | Sulfur content | 0 | 0 | 0 | 0 | 0 | 0 | 0 | 0 | 0 |
| | | Sulfated ash content | 0 | 0 | 0 | 0 | 0 | 0 | 0 | 0 | 0 |
| | Shell four-ball wear test | Wear scar diameter of fixed ball (mm) | 0.39 | 0.36 | 0.36 | 0.38 | 0.40 | 0.45 | 0.41 | 0.46 | 0.48 |
| | Reciprocating friction wear test | Wear scar width of test plate (mm) | 0.32 | 0.22 | 0.16 | 0.34 | 0.35 | 0.41 | 0.48 | 0.38 | 0.42 |
| | | Frictional coefficient | 0.129 | 0.112 | 0.109 | 0.133 | 0.131 | 0.143 | 0.141 | 0.147 | 0.143 |

| | | | Example | | | | | | | |
|---|---|---|---|---|---|---|---|---|---|---|
| | | | 10 | 11 | 12 | 13 | 14 | 15 | 16 | 17 |
| Lubricating oil composition | Blending amount (mass %) | Base oil | 99.00 | 99.00 | 99.00 | 99.00 | 99.00 | 99.00 | 99.00 | 99.00 |
| | | Zinc dialkyl dithiophosphate | 0.00 | 0.00 | 0.00 | 0.00 | 0.00 | 0.00 | 0.00 | 0.00 |
| | | Anti-wear Agent A | | | | | | | | |
| | | Anti-wear Agent B | | | | | | | | |
| | | Anti-wear Agent C | | | | | | | | |

TABLE 1-continued

| | | | | | | | | | | | |
|---|---|---|---|---|---|---|---|---|---|---|---|
| | | Anti-wear Agent D | | | | | | | | | |
| | | Anti-wear Agent E | | | | | | | | | |
| | | Anti-wear Agent F | | | | | | | | | |
| | | Anti-wear Agent G | | | | | | | | | |
| | | Anti-wear Agent H | 1.00 | | | | | | | | |
| | | Anti-wear Agent I | | 1.00 | | | | | | | |
| | | Anti-wear Agent J | | | 1.00 | | | | | | |
| | | Anti-wear Agent K | | | | 1.00 | | | | | |
| | | Anti-wear Agent L | | | | | 1.00 | | | | |
| | | Anti-wear Agent M | | | | | | 1.00 | | | |
| | | Anti-wear Agent N | | | | | | | 1.00 | | |
| | | Anti-wear Agent O | | | | | | | | 1.00 | |
| | | Total | 100.00 | 100.00 | 100.00 | 100.00 | 100.00 | 100.00 | 100.00 | 100.00 |
| Test result | property and the like of composition (mass %) | Phosphorous content | 0 | 0 | 0 | 0 | 0 | 0 | 0 | 0 |
| | | Sulfur content | 0 | 0 | 0 | 0 | 0 | 0 | 0 | 0 |
| | | Sulfated ash content | 0 | 0 | 0 | 0 | 0 | 0 | 0 | 0 |
| | Shell four-ball wear test | Wear scar diameter of fixed ball (mm) | 0.42 | 0.44 | 0.42 | 0.40 | 0.38 | 0.48 | 0.36 | 0.35 |
| | Reciprocating friction wear test | Wear scar width of test plate (mm) | 0.27 | 0.26 | 0.38 | 0.35 | 0.33 | 0.46 | 0.28 | 0.3 |
| | | Frictional coefficient | 0.12 | 0.09 | 0.145 | 0.140 | 0.128 | 0.148 | 0.125 | 0.126 |

| | | | Example | | | | | | | | |
|---|---|---|---|---|---|---|---|---|---|---|---|
| | | | 18 | 19 | 20 | 21 | 22 | 23 | 24 | 25 | 26 |
| Lubricating oil composition | Blending amount (mass %) | Base oil | 99.00 | 99.00 | 99.00 | 99.00 | 99.00 | 99.00 | 99.00 | 99.00 | 99.00 |
| | | Zinc dialkyl dithiophosphate | 0.00 | 0.00 | 0.00 | 0.00 | 0.00 | 0.00 | 0.00 | 0.00 | 0.00 |
| | | Anti-wear Agent P | 1.00 | | | | | | | | |
| | | Anti-wear Agent Q | | 1.00 | | | | | | | |
| | | Anti-wear Agent R | | | 1.00 | | | | | | |
| | | Anti-wear Agent S | | | | 1.00 | | | | | |
| | | Anti-wear Agent T | | | | | 1.00 | | | | |
| | | Anti-wear Agent U | | | | | | 1.00 | | | |
| | | Anti-wear Agent V | | | | | | | 1.00 | | |
| | | Anti-wear Agent W | | | | | | | | 1.00 | |
| | | Anti-wear Agent X | | | | | | | | | 1.00 |
| | | Anti-wear Agent Y | | | | | | | | | |
| | | Anti-wear Agent Z | | | | | | | | | |
| | | Anti-wear Agent AA | | | | | | | | | |
| | | Anti-wear Agent AB | | | | | | | | | |
| | | Anti-wear Agent AC | | | | | | | | | |
| | | 2-(aminomethyl) pyridine | | | | | | | | | |
| | | Total | 100.00 | 100.00 | 100.00 | 100.00 | 100.00 | 100.00 | 100.00 | 100.00 | 100.00 |
| Test result | property and the like of composition (mass %) | Phosphorous content | 0 | 0 | 0 | 0 | 0 | 0 | 0 | 0 | 0 |
| | | Sulfur content | 0 | 0 | 0 | 0 | 0 | 0 | 0 | 0 | 0 |
| | | Sulfated ash content | 0.01 | 0.03 | 0 | 0 | 0 | 0 | 0 | 0 | 0 |
| | Shell four-ball wear test | Wear scar diameter of fixed ball (mm) | 0.35 | 0.35 | 0.39 | 0.43 | 0.42 | 0.37 | 0.39 | 0.48 | 0.47 |
| | Reciprocating friction wear test | Wear scar width of test plate (mm) | 0.14 | 0.3 | 0.22 | 0.45 | 0.42 | 0.31 | 0.29 | 0.4 | 0.42 |
| | | Frictional coefficient | 0.107 | 0.118 | 0.126 | 0.146 | 0.145 | 0.134 | 0.138 | 0.162 | 0.148 |

| | | | Example | | | | | Comparative Example | | |
|---|---|---|---|---|---|---|---|---|---|---|
| | | | 27 | 28 | 29 | 30 | 31 | 1 | 2 | 3 |
| Lubricating oil composition | Blending amount (mass %) | Base oil | 99.00 | 99.00 | 99.00 | 99.00 | 99.00 | 100.00 | 98.78 | 99.00 |
| | | Zinc dialkyl dithiophosphate | 0.00 | 0.00 | 0.00 | 0.00 | 0.00 | 0.00 | 1.22 | |
| | | Anti-wear Agent P | | | | | | | | |
| | | Anti-wear Agent Q | | | | | | | | |
| | | Anti-wear Agent R | | | | | | | | |
| | | Anti-wear Agent S | | | | | | | | |
| | | Anti-wear Agent T | | | | | | | | |
| | | Anti-wear Agent U | | | | | | | | |
| | | Anti-wear Agent V | | | | | | | | |
| | | Anti-wear Agent W | | | | | | | | |

TABLE 1-continued

|  |  |  |  |  |  |  |  |  |  |
|---|---|---|---|---|---|---|---|---|---|
|  | Anti-wear Agent X |  |  |  |  |  |  |  |  |
|  | Anti-wear Agent Y | 1.00 |  |  |  |  |  |  |  |
|  | Anti-wear Agent Z |  | 1.00 |  |  |  |  |  |  |
|  | Anti-wear Agent AA |  |  | 1.00 |  |  |  |  |  |
|  | Anti-wear Agent AB |  |  |  | 1.00 |  |  |  |  |
|  | Anti-wear Agent AC |  |  |  |  | 1.00 |  |  |  |
|  | 2-(aminomethyl) pyridine |  |  |  |  |  |  |  | 1.00 |
| Test result | property and the like of composition (mass %) | Total | 100.00 | 100.00 | 100.00 | 100.00 | 100.00 | 100.00 | 100.00 | 100.00 |
|  |  | Phosphorous content | 0 | 0 | 0 | 0 | 0 | 0 | 0.10 | 0 |
|  |  | Sulfur content | 0 | 0 | 0 | 0 | 0 | 0 | 0.21 | 0 |
|  |  | Sulfated ash content | 0.01 | 0 | 0.01 | 0 | 0.01 | 0 | 0.24 | 0 |
|  | Shell four-ball wear test | Wear scar diameter of fixed ball (mm) | 0.43 | 0.35 | 0.37 | 0.36 | 0.38 | 0.58 | 0.45 | 0.56 |
|  | Reciprocating friction wear test | Wear scar width of test plate (mm) | 0.33 | 0.32 | 0.23 | 0.27 | 0.25 | 0.54 | 0.44 | 0.52 |
|  |  | Frictional coefficient | 0.148 | 0.127 | 0.117 | 0.138 | 0.135 | 0.171 | 0.166 | 0.165 |

TABLE 2

|  |  |  | Example | Comparative Example |  |
|---|---|---|---|---|---|
|  |  |  | 32 | 4 | 5 |
| Lubricating Oil composition | Blending amount (mass %) | Base oil | 95.44 | 96.44 | 95.22 |
|  |  | Metal-based detergent | 2.56 | 2.56 | 2.56 |
|  |  | Polybutenyl succinimide | 1.00 | 1.00 | 1.00 |
|  |  | Zinc dialkyl dithiophosphate | 0.00 | 0.00 | 1.22 |
|  |  | Anti-wear Agent A | 1.00 | 0.00 | 0.00 |
|  |  | Total | 100.00 | 100.00 | 100.00 |
|  | Properties and the like of composition (mass %) | Phosphorous content | 0 | 0 | 0.10 |
|  |  | Sulfur content | 0 | 0 | 0.22 |
|  |  | Calcium content | 0.20 | 0.20 | 0.20 |
|  |  | Sulfated ash content | 0.65 | 0.65 | 0.89 |
| Test result | Shell four-ball wear test | Wear scar diameter of fixed ball (mm) | 0.34 | 0.44 | 0.34 |
|  | Reciprocating friction wear test | Wear scar width of test plate(mm) | 0.30 | 0.35 | 0.32 |
|  |  | Frictional coefficient | 0.103 | 0.113 | 0.113 |
|  | Oxidative stability test | Base number of new oil (hydrochloric acid method) mgKOH/g | 6.53 | 5.91 | 6.08 |
|  |  | Base number after test (hydrochloric acid method) mgKOH/g | 1.69 | 3.50 | 0.38 |
|  |  | Residual ratio of base number (%) | 25.9 | 59.2 | 6.3 |

INDUSTRIAL APPLICABILITY

The mineral oil-based hydrocarbon oil or synthetic lubricating base oil, or a mixture thereof each obtained by blending the anti-wear agent of the present invention has improved wear resistance in an internal combustion engine or a transmission engine for drive system and exhibit excellent friction-reducing property and base number-retaining property.

The invention claimed is:

1. A lubricating oil composition comprising an anti-wear agent, said anti-wear agent comprising:
   a reaction product of a heterocyclic compound and a compound selected from the group consisting of a boron compound and a molybdenum compound;
   wherein the heterocyclic compound is represented by formula (I) and optionally contains a double bond in a ring part:

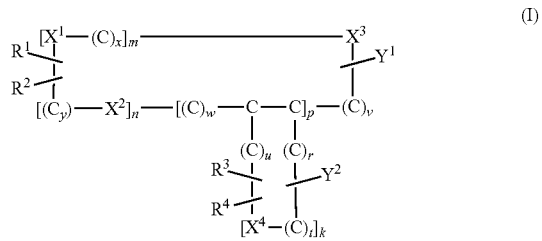

wherein
$X^1$, $X^2$, $X^3$, and $X^4$ each independently represent N, NH, O, or S; p represents 0 or 1; x and y each independently represent an integer of 0 to 2; u and r each independently represent an integer of 0 to 3; t and w each independently represent an integer of 0 to 3; n and m each independently represent 0 or 1; and k represents an integer of 0 to 3; provided that $X^1$, $X^2$, $X^3$, $X^4$, x, y, u, r, t and w are selected such that a base skeleton of the heterocycle of formula (I) is a benzoimidazole, indazole, triazine, or triazole;

$R^1$ to $R^4$ each independently represent a hydrogen atom bound to a carbon atom, or a hydrocarbon group which may have at least one kind of substituent selected from the group consisting of an amino group, an amide group, an ether group, and a carboxyl group, each substituent being bound to a carbon atom; provided that if p represents 0, $R^1$ and $R^2$ do not represent a hydrogen atom simultaneously, and if p represents 1, $R^1$ to $R^4$ do not represent a hydrogen atom simultaneously;

$Y^1$ and $Y^2$ each independently represent a hydrogen atom, a halogen atom, a functional group selected from the group consisting of an amino group, an amide group, a hydroxy group, a carbonyl group, an aldehyde group, a carboxyl group, an ester group, and an ether group, or a hydrocarbon group which may have at least one kind of functional group selected from the functional groups and has a total in carbon atoms of 1 to 150;

the reaction product is a reaction product of the heterocyclic compound having a base skeleton of a benzoimidazole, triazole, triazine, or indazole and the boron compound, or the reaction product is a reaction product of the heterocyclic compound having a base skeleton of a triazine or indazole and the molybdenum compound; and a blending amount of the anti-wear agent is 0.1 to 10 mass % based on the total amount of the lubricating oil composition.

2. The lubricating oil composition according to claim 1, wherein the lubricating oil composition has a zinc content of 600 ppm by mass or less in terms of the element based on a total amount of the lubricating oil composition.

3. The lubricating oil composition according to claim 1, wherein the lubricating oil composition has a phosphorous content of 500 ppm by mass or less in terms of the element based on a total amount of the lubricating oil composition.

4. The lubricating oil composition according to claim 1, wherein the lubricating oil composition is for an internal combustion engine.

5. The lubricating oil composition according to claim 1, wherein the reaction product is a reaction product of the heterocyclic compound having a base skeleton of a benzoimidazole, triazole, triazine, or indazole and the boron compound.

6. The lubricating oil composition according to claim 1, wherein the reaction product is a reaction product of the heterocyclic compound having a base skeleton of a triazine or indazole and the molybdenum compound.

* * * * *